(12) United States Patent
Chuter et al.

(10) Patent No.: US 8,262,718 B2
(45) Date of Patent: Sep. 11, 2012

(54) ASSEMBLY FOR CONTROLLED SEQUENTIAL STENT GRAFT DEPLOYMENT

(75) Inventors: Timothy A. Chuter, San Francisco, CA (US); Michael Lawrence-Brown, City Beach (AU); David E. Hartley, Subiaco (AU)

(73) Assignees: William A. Cook Australia Pty. Ltd., Queensland (AU); Cook Medical Technologies LLC, Bloomington, IN (US)

( * ) Notice: Subject to any disclaimer, the term of this patent is extended or adjusted under 35 U.S.C. 154(b) by 1538 days.

(21) Appl. No.: 11/789,944

(22) Filed: Apr. 26, 2007

(65) Prior Publication Data
US 2007/0260301 A1    Nov. 8, 2007

Related U.S. Application Data

(66) Substitute for application No. 60/795,617, filed on Apr. 27, 2006.

(60) Provisional application No. 60/795,634, filed on Apr. 27, 2006.

(51) Int. Cl.
*A61F 2/06* (2006.01)

(52) U.S. Cl. ...................................... 623/1.11

(58) Field of Classification Search ......... 623/1.11–1.12
See application file for complete search history.

(56) References Cited

U.S. PATENT DOCUMENTS

| 6,764,503 | B1 * | 7/2004 | Ishimaru | 623/1.11 |
| 2003/0233140 | A1 | 12/2003 | Hartley et al. | |
| 2004/0098079 | A1 * | 5/2004 | Hartley et al. | 623/1.11 |
| 2005/0154443 | A1 * | 7/2005 | Linder et al. | 623/1.11 |

FOREIGN PATENT DOCUMENTS

| WO | WO 98/53761 | 12/1998 |
| WO | WO 99/25280 | 5/1999 |
| WO | WO 03/101518 | 12/2003 |
| WO | WO 2006/007389 | 1/2006 |

* cited by examiner

*Primary Examiner* — Gary Jackson
*Assistant Examiner* — Eric Blatt
(74) *Attorney, Agent, or Firm* — Richard J. Godlewski

(57) ABSTRACT

A stent graft introducer (1) which includes a handle arrangement which by telescopic movement of a slide or slide portions (104, 106) into a handle portion (100) causes controlled sequential deployment of a stent graft (14). Stops (218, 217, 218, 219) ensure actions are carried out in a selected order. A sheath (116) of the introducer is fixed to a slide portion such that with retraction of the slide portion the sheath is withdrawn from a stent graft retained on the introducer and at a selected position trigger wires retaining the stent graft onto the introducer are also released. Interconnections between the slides and the handle are provided to prevent relative rotation and re-extension after full retraction.

16 Claims, 16 Drawing Sheets

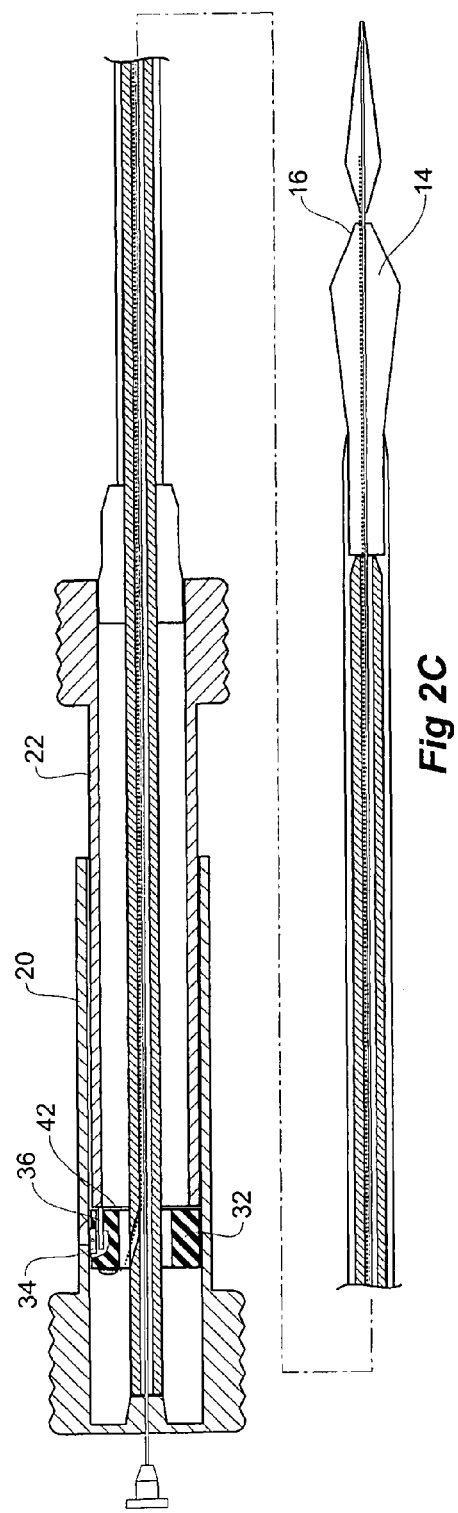
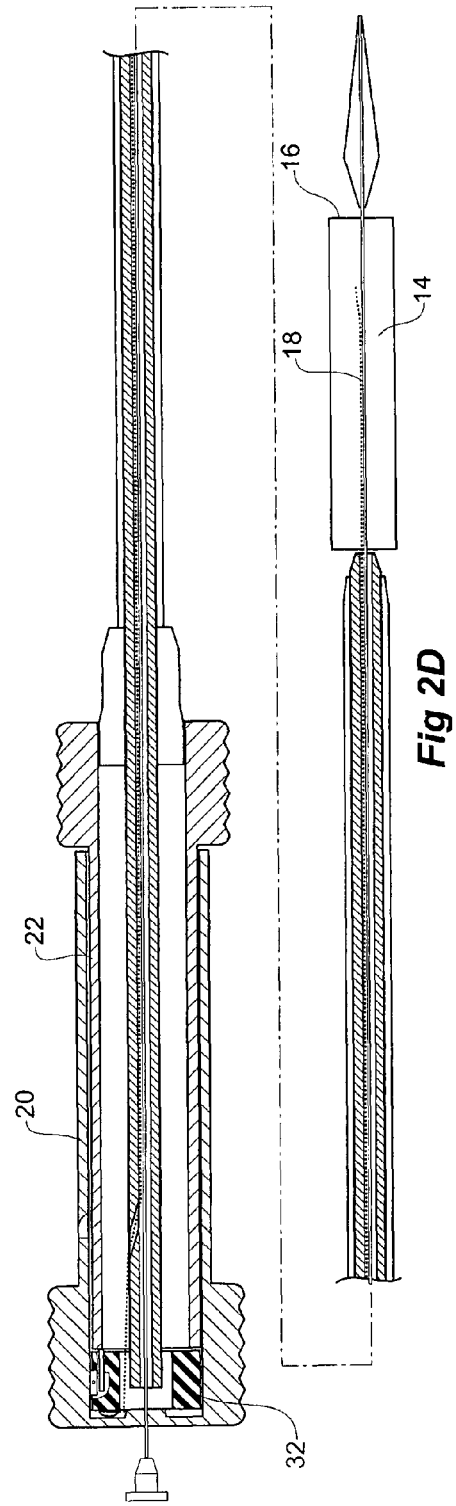
Fig 2C
Fig 2D

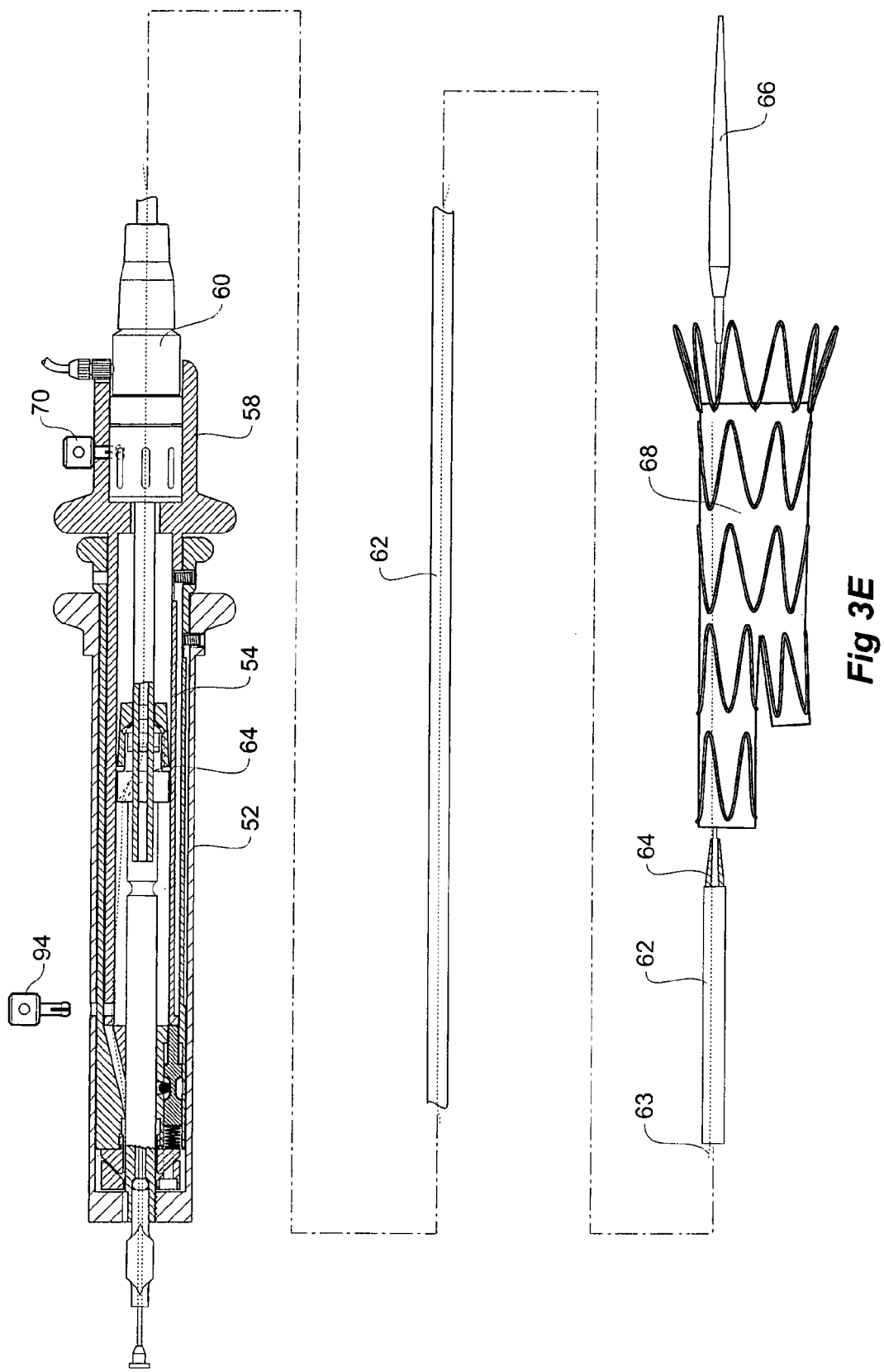

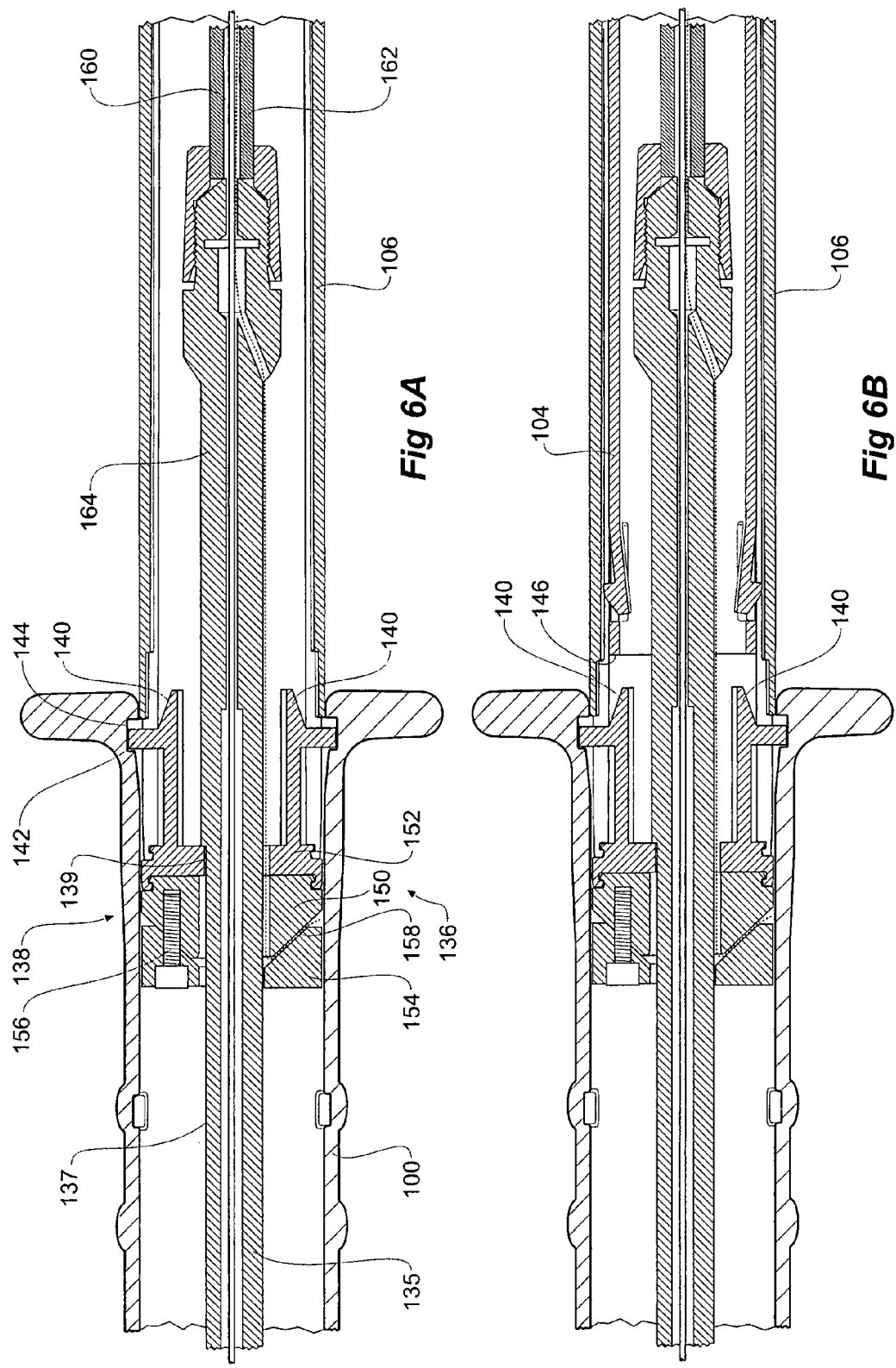

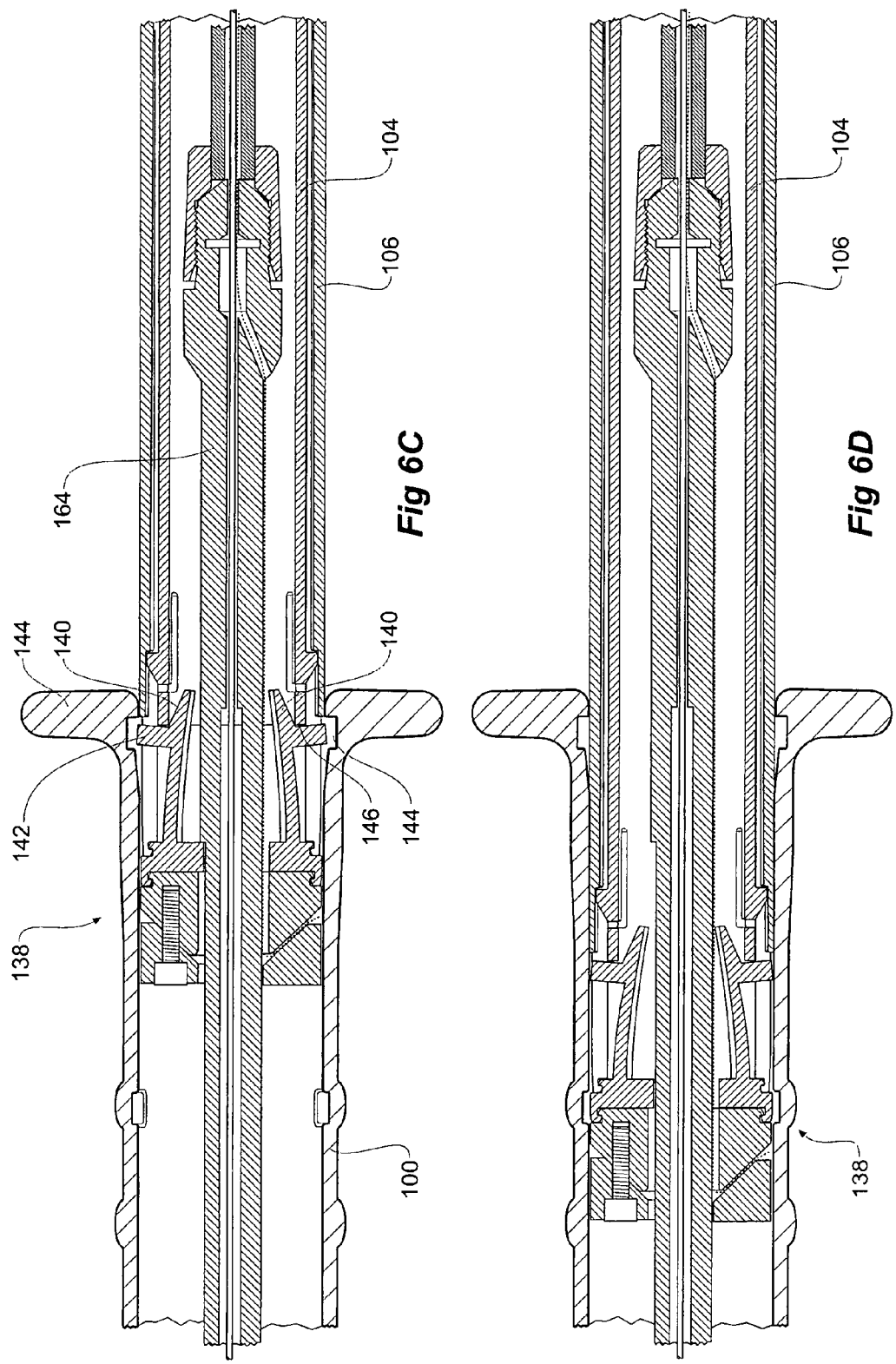

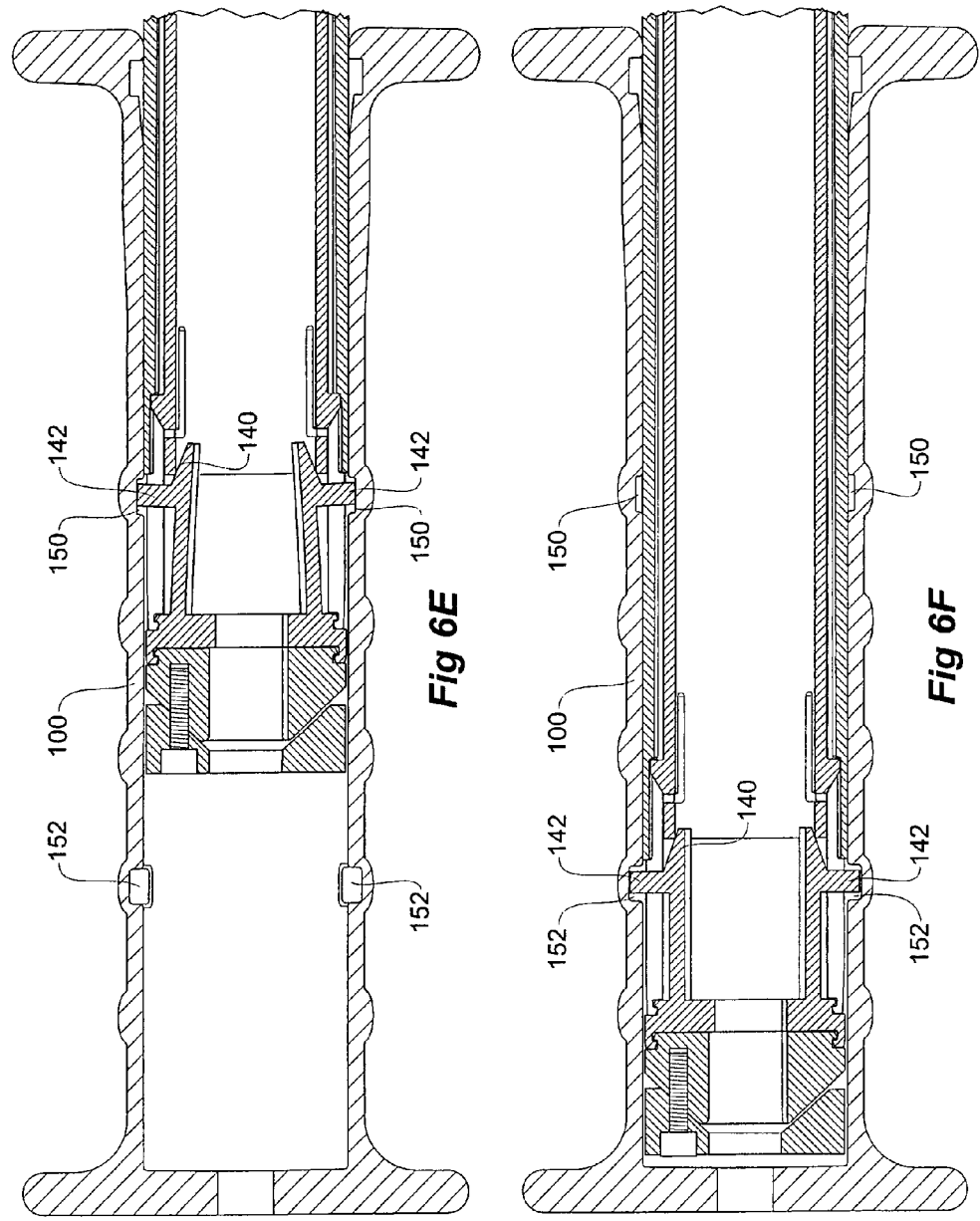

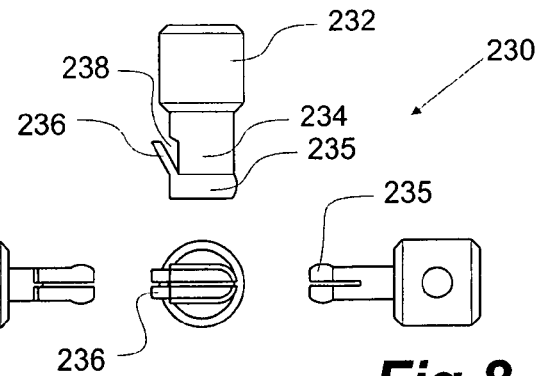
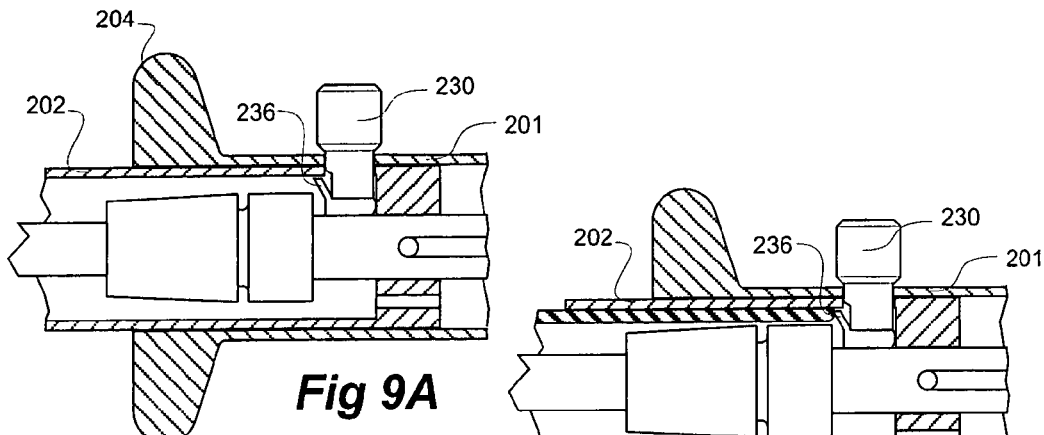
Fig 8
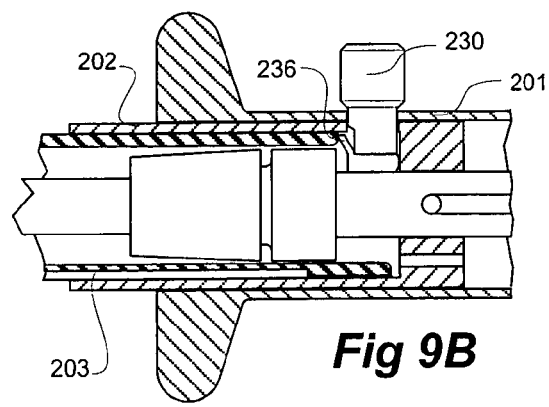
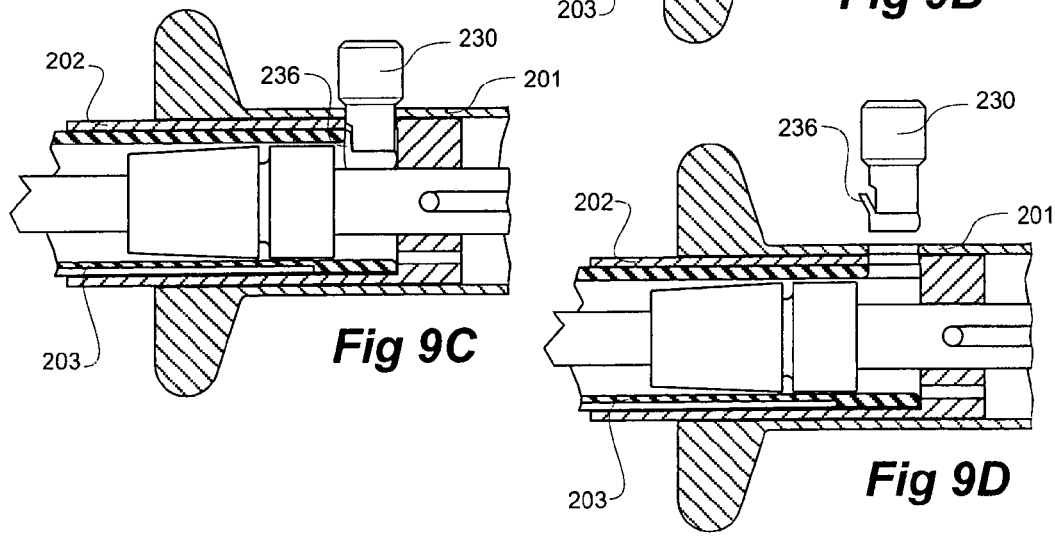
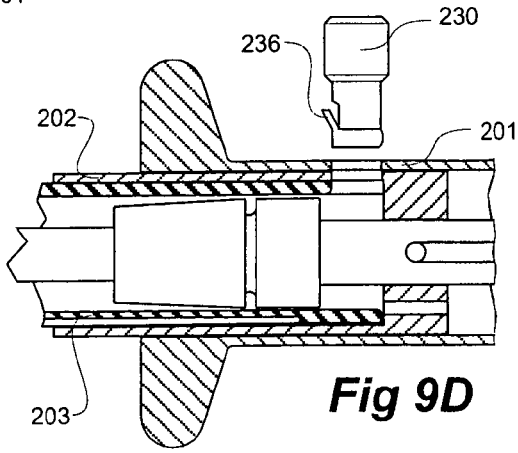

ASSEMBLY FOR CONTROLLED SEQUENTIAL STENT GRAFT DEPLOYMENT

CROSS-REFERENCE TO RELATED APPLICATIONS

This application is related to and claims priority from U.S. Provisional Patent Specification No. 60/795,617 filed Apr. 27, 2006 entitled "Controlled Sequential Deployment" the contents of which are incorporated in their entirety herein and for all purposes. This application is also related to U.S. Provisional Patent Specification No. 60/795,634 filed Apr. 27, 2006 entitled "Rotary Handle for Controlled Sequential Deployment" the contents of which are incorporated in their entirety herein and for all purposes.

INCORPORATION BY REFERENCE

The following co-pending patent applications are referred to in the following description:

PCT Patent Publication No. WO 98/53761 entitled "A Prosthesis And A Method And Means Of Deploying A Prosthesis" discloses an introducer for a prosthesis which retains the prosthesis so that each end can be moved independently. These features and other features disclosed in PCT Patent Publication No. WO 98/53761 could be used with the present invention and the disclosure of PCT Patent Publication No. WO 98/53761 is herewith incorporated in its entirety into this specification.

U.S. Provisional Patent Application Ser. No. 60/392,682, filed Jun. 28, 2002, U.S. patent application Ser. No. 10/447,406, filed May 29, 2003, and Published on Dec. 18, 2003, as U.S. Patent Application Publication No. US-2003-0233140-A1 entitled "Trigger Wire System", and PCT Patent Publication No. WO 03/101518 entitled "Trigger Wire System For A Prosthesis Deployment Device" disclose release wire systems for the release of stent grafts retained on introducer devices. This feature and other features disclosed in U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 could be used with the present invention and the disclosure of U.S. Provisional Patent Application Ser. No. 60/392,682, U.S. patent application Ser. No. 10/447,406, and U.S. Patent Application Publication No. US-2003-0233140-A1, and PCT Patent Publication No. WO 03/101518 is herewith incorporated in its entirety into this specification

TECHNICAL FIELD

This invention relates to a medical device and more particularly to a device for endovascular deployment of a stent graft.

BACKGROUND OF THE INVENTION

In our earlier patent application, PCT Patent Publication No. WO 98/53761 entitled "A Prosthesis and a Method Deploying a Prosthesis" there is disclosed an introducer for a stent graft which retains the stent graft so that each end can be moved and released independently during the process of endovascular deployment of the stent graft. This device requires that a number of actions be taken in a particular consecutive order to place a stent graft in the required position in the vasculature and then release one end of the stent graft and then another end and if required, between the release of each of the ends, the placement of a branch stent graft into a side arm of the stent graft. These features and other features disclosed in PCT Patent Publication No. WO 98/53761 are incorporated herewith in their entirety into this specification.

It is desirable that the set of sequential actions necessary to release the stent graft at the desired position in the vasculature be undertaken in the required order and that there be less chance for operator error during such a deployment.

It is the object of this invention therefore to provide a deployment device which is arranged to introduce, deploy and release a stent graft by a series of sequential actions.

SUMMARY OF THE INVENTION

In one form therefore, although this may not necessarily be the only or broadest form, the invention is said to reside in a stent graft introducer comprising a deployment catheter and a handle assembly; the deployment catheter comprising a pusher, a stent graft releasably retained onto the pusher, a temporary stent graft retention arrangement, a sheath coaxially around the pusher and enclosing the stent graft and a sheath hub to which the sheath is mounted; the handle assembly comprising, a handle, a first slide and a second slide, the first slide able to slide to retract within the second slide and the second slide able to slide to retract within the handle, the first slide including a releasable engagement arrangement to engage and retain the sheath hub thereon, a first removable stop pin arrangement engaged between the handle and the second slide to prevent relative movement thereof, the pusher extending longitudinally through the first and second slides and being mounted to the handle, the temporary stent graft retention arrangement including trigger wires extending through the pusher and being affixed to the second slide; whereby movement of the first slide with respect to the second slide moves the sheath hub and thereby the sheath on the pusher to expose the stent graft until the first slide engages against the first removable stop pin arrangement and whereupon removal of the first removable stop pin arrangement the second slide can move with respect to the handle thereby withdrawing the trigger wires and releasing the temporary stent graft retention arrangement.

There may further be a second removable stop pin arrangement between the first slide and the second slide to prevent relative movement thereof until it is removed.

There may further be a third removable stop pin arrangement between the handle and the second slide to restrict the distance of retraction of the second slide into the handle until the third removable stop pin arrangement has been removed.

Preferably the first removable stop pin arrangement engaged between the handle and the second slide comprises a catch on the second slide engaged into a recess on the handle and the catch is disengaged by the first slide engaging against the catch upon complete retraction of the first slide into the second slide.

Preferably the sheath hub includes a protrusion thereon and the releasable engagement arrangement to engage and retain the hub within the first slide comprises hook arrangement to engage around the protrusion.

There may further be means to prevent relative rotation of the first slide with respect to the second slide. There may further be means to prevent re-extension of the first slide with respect to the second slide after complete retraction. There may further be means to prevent relative rotation of the second slide with respect to the handle. There may further be means to prevent re-extension of the second slide with respect to the handle after complete retraction.

In one embodiment the first removable stop pin is manually actuatable. In an alternative embodiment the first removable stop pin can be automatically actuated by engagement of the first slide with the first removable stop pin.

In an alternative form the invention comprises a stent graft introducer controlled sequential deployment arrangement comprising a first movement stage in which a sheath is partially withdrawn from a stent graft retained on the introducer, a second movement stage in which the sheath continues to be withdrawn and a release arrangement partially releases the stent graft from the introducer and a third movement stage in which the sheath is completely withdrawn from the stent graft and the stent graft is fully released from the introducer, the movement stages being arranged such that the second movement stage cannot occur until the first movement stage has been completed.

In an alternative form the invention comprises a stent graft introducer actuation assembly comprising a fixed handle, a release portion and a sliding handle, the release portion telescoping within the fixed handle and the sliding handle telescoping within the release portion, the sheath hub being retained to the sliding handle and the pusher extending from the fixed handle through the release portion and the sliding handle, a first stop pin to prevent movement of the sliding handle with respect to the release portion and a second stop pin to prevent movement of the release portion with respect to the fixed handle.

There may further be a third stop pin acting between the fixed handle and the release portion to restrict the distance of retraction of the release portion into the fixed handle until the third stop pin is removed.

Preferably the fixed handle includes a first grip and the sliding handle includes a second grip.

There may further be a means to prevent relative rotation of the sliding handle with respect to the release portion. There may further be a means to prevent re-extension of the sliding handle with respect to the release portion after complete retraction of the sliding handle into the release portion. There may further be a means to prevent relative rotation of the release portion with respect to the fixed handle. There may further be a means to prevent re-extension of the release portion with respect to fixed the handle after complete retraction of the release portion into the fixed handle.

In an alternative form the invention comprises a stent graft introducer comprising a deployment catheter and a handle assembly; the deployment catheter comprising a pusher, a stent graft releasably retained onto the pusher, a stent graft retention arrangement, a sheath coaxially around the pusher and enclosing the stent graft and a sheath hub to which the sheath is mounted, a guide wire catheter extending from distal of the handle to a nose cone dilator, the sheath hub including a protrusion and the releasable engagement arrangement to engage and retain the hub within the first slide comprises hook arrangement to engage around the protrusion; the handle assembly comprising, a handle, a first slide and a second slide, the first slide able to slide to retract within the second slide and the second slide able to slide to retract within the handle, the first slide including a releasable engagement arrangement to engage and retain the sheath hub therein, a first removable stop pin engaged between the handle and the second slide to prevent relative movement thereof, the first removable stop pin being disengaged by the first slide engaging against the first removable stop pin when fully retracted within the second slide, a second removable stop pin between the first slide and the second slide to prevent relative movement thereof until it is removed, a third removable stop pin to restrict the distance of retraction of the second slide into the handle until the third removable stop pin has been removed, the pusher extending longitudinally through the first and second slides and being mounted to the handle, the stent graft retention arrangement including trigger wires extending through the pusher and being affixed to the second slide; whereby movement of the first slide with respect to the second slide moves the sheath hub and thereby the sheath on the pusher to expose the stent graft until the first slide engages against and releases the first removable stop pin such that the second slide can move with respect to the handle thereby withdrawing the trigger wires and releasing the stent graft retention arrangement, the sheath hub including a protrusion and the releasable engagement arrangement to engage and retain the hub within the first slide comprises hook arrangement to engage around the protrusion, the first removable stop pin engaged between the handle and the second slide to prevent relative movement thereof comprises a catch on the second slide engaged into a recess on the handle and the catch is disengaged by the first slide engaging against the catch, means to prevent relative rotation of the first slide with respect to the second slide, means to prevent re-extension of the first slide with respect to the second slide after complete retraction, means to prevent relative rotation of the second slide with respect to the handle and means to prevent re-extension of the second slide with respect to the handle after complete retraction.

In an alternative form the invention comprises a stent graft introducer actuation assembly comprising a fixed handle, a release portion and a sliding handle, the release portion telescoping within the fixed handle and the sliding handle telescoping within the release portion, the sheath hub being retained to the sliding handle and the pusher extending from the fixed handle through the release portion and the sliding handle, a first stop pin to prevent movement of the sliding handle with respect to the release portion and a second stop pin to prevent movement of the release portion with respect to the fixed handle, a third stop pin acting between the fixed handle and the release portion to restrict the distance of retraction of the release portion into the fixed handle until the third stop pin is removed, the fixed handle including a first grip and the sliding handle includes a second grip, means to prevent relative rotation of the sliding handle with respect to the release portion, means to prevent re-extension of the sliding handle with respect to the release portion after complete retraction of the sliding handle into the release portion, means to prevent relative rotation of the release portion with respect to the fixed handle and means to prevent re-extension of the release portion with respect to fixed the handle after complete retraction of the release portion into the fixed handle.

The stent graft introducer according to the present invention may be able to be actuated manually or it may be actuated by a rack and pinion, worm, cable or lead screw drive which can be driven using a winding handle or by an electric motor. The use of an electric motor drive may give improved control as the physician does not need to exert excessive force to slide the various components.

It will be seen that by the various forms of this invention, a device is provided which by the action of holding one portion of the deployment device and moving another portion of the deployment device in a linear sliding motion, the various sequential actions necessary to release the stent graft can occur.

BRIEF DESCRIPTION OF THE DRAWING

This then generally describes the invention but to assist with understanding, reference will now be made to the accompanying drawings which show preferred embodiments of the invention.

In the drawings:

FIGS. 2A to 2D show the sequential action deployment device of FIG. 1 in cross-section with the various actions and stages of the deployment illustrated;

FIGS. 3A to 3E show a longitudinal cross-sectional view of an alternative embodiment of sequential action introducer and in particular, a device suitable for deploying a branched stent graft;

FIGS. 6A to 6F show details of the locking mechanism of the embodiment shown in FIG. 4;

FIG. 8 shows one embodiment of pin suitable for the stop between the first slide and the second slide; and FIGS. 9A to 9D show the various stage of the slide action using the pin shown in FIG. 8;

DETAILED DESCRIPTION

Figure 1A:
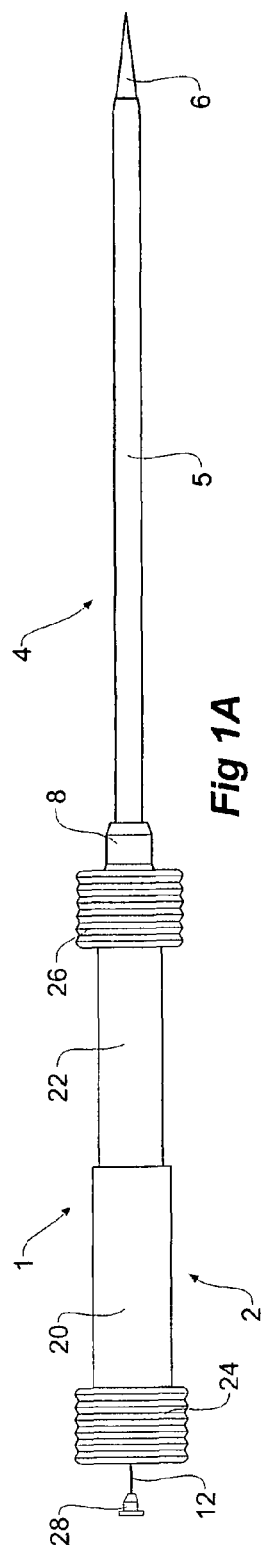
FIGS. 1A to 1D show the various sequential steps for the releasing of a stent graft using one embodiment of a sequential action deployment device according to the present invention.
Figure 1B:
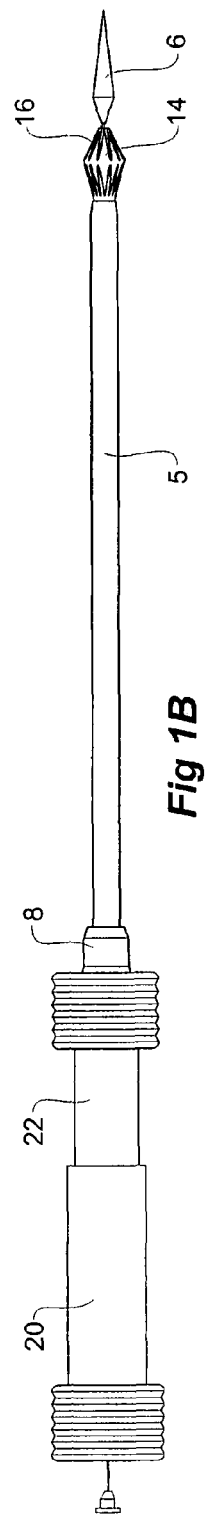
Figure 1C:
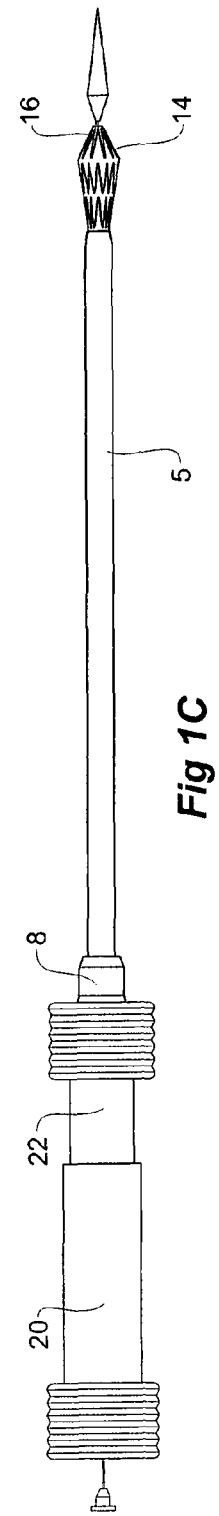
Figure 1D:
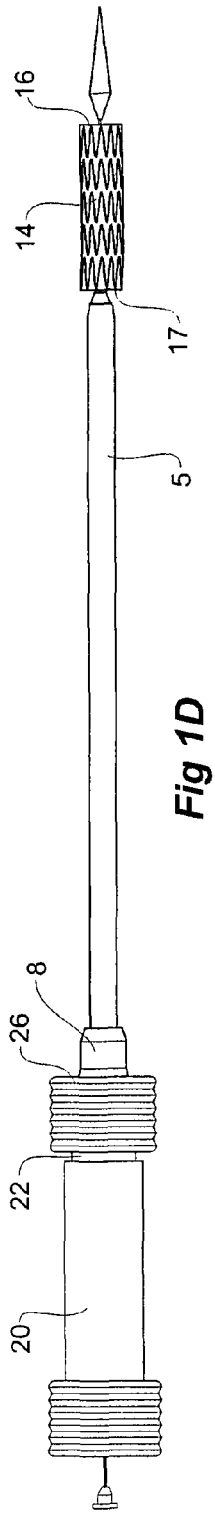
Figure 2A:
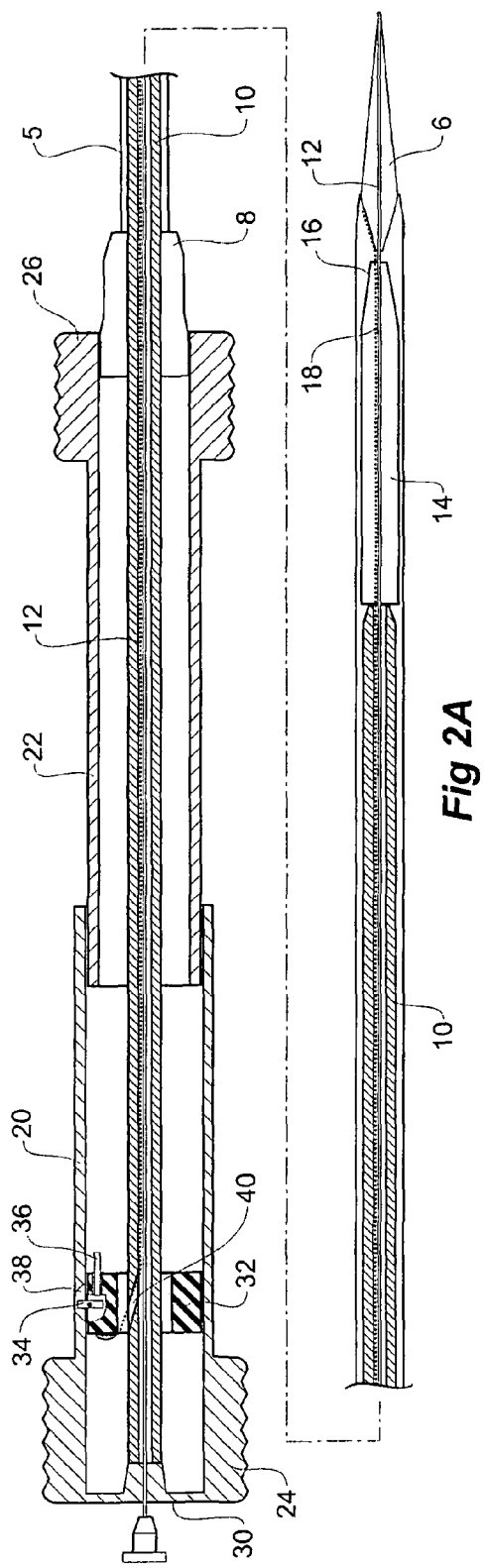

Now looking at the first embodiments shown in FIGS. 1A to 1D and 2A to 2D, it will be seen that the introducer 1 generally comprises a handle assembly 2 and an introduction assembly 4. In use, the handle assembly 2 remains outside of the patient and the introduction assembly 4 is deployed into a patient using the Seldinger technique. The introduction section 4 comprises a nose cone dilator 6, a sheath 5 extending from a sheath hub 8 to the nose cone and under the sheath as can be seen in FIG. 2A, a pusher catheter 10 and a guide wire catheter 12 which extends to the nose cone 6. In the region between the pusher catheter 10 and the nose cone dilator 6, a stent graft 14 is carried. There is a retention arrangement for the proximal end 16 of the stent graft which includes a trigger wire 18. The trigger wire extends back into the handle assembly 2, as will be discussed below, through a lumen in the pusher catheter 10.

The handle assembly consists of a handle portion 20 and a sliding portion 22. The handle portion 20 has a grip 24 and the sliding portion has a grip 26. The hub 8 of the sheath 5 is retained into the grip 26 (by means not shown). Extending out of the distal end of the handle portion 20 is the guide wire catheter 12 and on the distal end of the guide wire catheter 12 is a male Luer lock connector 28. The Luer lock connector 28 can be used to enable the flushing of any foreign substance that may be present in the guide wire catheter 12 prior to insertion of the device onto a guide wire during deployment and where necessary to enable contrast fluids to be supplied through the guide wire catheter 12 to the nose cone dilator 6 to enable an operator to inject contrast medium to assist with radiographic positioning of the stent graft during deployment.

As can particularly be seen in FIGS. 2A to 2D, the pusher catheter 10 extends back to the distal end 30 of the handle portion 20 and is affixed thereto. Within the fixed handle portion 20 is a slider 32 which is retained in position by means of a locking arm 34. The locking arm 34 can be released by release pin 36 pressing on the locking arm and releasing it from recess 38 in the wall of the handle portion 20.

Now looking at the sequence of operations with respect to FIGS. 1A to 1D, it will be noted that in FIG. 1A, the sheath 5 extends forward to the nose cone dilator 6 and covers the stent graft which is retained distally of the nose cone dilator. In a first stage of operation as shown in FIG. 1B, the handle portion 20 is held stationary and the slider portion 22 is moved towards the handle portion 20 to telescopically move inside the handle portion 20. As the hub 8 is retained to the slider portion 22 and the sleeve 5 is retained to the hub, this action withdraws the sleeve from the nose cone dilator 6 which exposes the stent graft 14. At this stage, however, the proximal end of the stent graft 16 is still retained just distally of the nose cone dilator 6.

As shown in FIG. 1C continued movement of the sliding portion 22 with respect to the handle portion 20 continues to release the stent graft 14 from its constriction by the sheath 5. At this stage, movement of the handle 20 by rotation or longitudinal movement can be used to accurately position the stent graft 14 and particularly the proximal end 16 with respect to adjacent vasculature.

As shown in FIG. 1D continued movement of the sliding portion 22 with respect to the handle portion 20 can occur until the grip portion 26 has engaged the handle portion 20. At this stage, sheath 5 is fully withdrawn from the stent graft 14 and the distal end 17 of the stent graft has fully expanded and also the release arrangement for the proximal end 16 has also released, as will be discussed below, thereby completely freeing the stent graft 14 so that it can expand by use of its self-expanding stents against the wall of the vasculature into which it is deployed.

In a third stage of the deployment process the deployment device can be retracted either completely or by releasing the hub of the sheath from the sliding portion and withdrawing the pusher and nose cone dilator through the lumen of the stent graft and leaving the sheath and hub in place for further endovascular processes.

FIGS. 2A to 2D show in longitudinal cross section equivalent stages in the release procedure for the stent graft as FIGS. 1A to 1D.

As can be seen in FIG. 2A, the stent graft 14 is completely enclosed by the sheath 5 which extends forward to the nose cone dilator 6 and the proximal end 16 is retained in a constrained condition, just distal of the nose cone dilator 6. Movement of the trigger wire 18 will release the retention of the proximal end 16 of the stent graft 14.

The trigger wire 18 shown dotted extends back through the lumen of the pusher 10 and exits the pusher catheter through aperture 40 and is fastened to the slider 32.

Figure 2B:
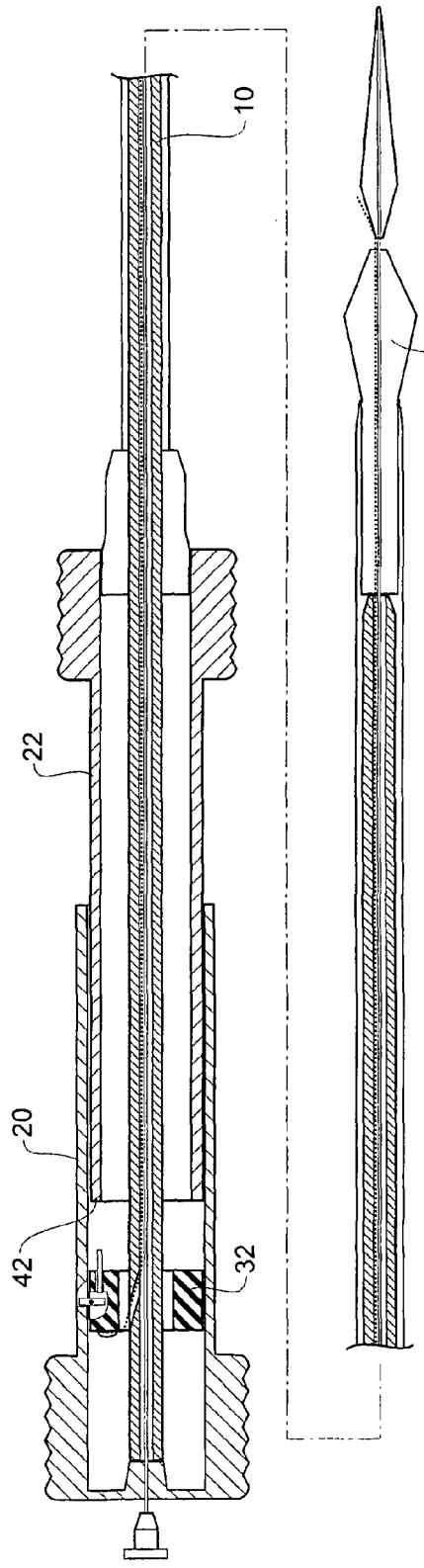

In the first stage of movement of the sliding portion 22 into the handle 20 in a telescopic manner, it will be noted that the stent graft 14 starts to be exposed, as shown in FIG. 2B but that at this stage, the distal end 42 of the slider portion 20 has not yet reached the slider 32.

Subsequent movement of the sliding portion 22 into the handle 20 as shown in FIG. 2C causes the distal end 42 of the slider portion 22 to engage the release pin 36 in the slider 32 which rotates the release arm 34 from its engagement into the wall of the handle portion 20 so that the slider is not locked in position within the handle portion 20. At this stage, the stent graft 14 is more exposed but is still retained at its distal end 16.

Still further movement of the sliding portion 22 into the handle portion also moves the slider 32 within the handle portion 20 and this pulls the trigger wire 18 so that it releases the proximal end 16 of the stent graft 14.

It will be seen that by the stylised set of actions, the stent graft is uncovered and released without the operator having to take a certain action at a certain time. It will be realised too that the action can be done as a single stroke or can be done in stages with the operator injecting contrast medium through the guide wire catheter to observe the position of the stent graft before the complete release of the stent graft.

FIGS. 3A to 3E show cross-sectional views of an alternative embodiment of stent graft introducer according to the present invention. This embodiment will be discussed with respect to the deployment of a bifurcated stent graft having a longer leg and a shorter leg. This embodiment can, however, be used with other forms of stent graft such as fenestrated stent grafts.

In this embodiment, the handle assembly 50 comprises a handle portion 52, a first slide 54 and a second slide 56. The first slide 54 has a hub retention socket 58 and into this is received the hub 60 of a stent graft introduction assembly. A sheath 62 is mounted to the hub 60 and extends forward to a nose cone dilator 66. Just distal of the nose cone dilator a stent graft 68 is retained. A trigger wire 63 or a set of trigger wires engages with the exposed stent 69 at the proximal end of the stent graft and retains the proximal end to the guide wire catheter. The trigger wire or wires extend distally through the guide wire catheter lumen of the pusher catheter 64 to the trigger wire clamp 76 at the distal end of the second slide 56.

A method of retention of the proximal end of a stent graft onto a introducer is disclosed in PCT Publication WO03/101518 entitled "Trigger Wire System for a Prosthesis Deployment Device". This feature and other features disclosed in PCT Publication WO03/101518 could be used with the present invention and the disclosure of PCT Publication WO03/101518 is herewith incorporated in its entirety into this specification.

The hub 60 is retained in the hub socket 58 on the first slide 54 by means of a locking pin 70.

The pusher catheter 64 extends back through the hub 60 to a mounting post 72 within the handle portion 52. The first slide 54 slides within the second slide 56 and a locking pin 74 prevents relative movement of the first slide within the second slide until the locking pin 74 has been removed. The second slide 56 includes the trigger wire clamp 76 at the distal end thereof and a locking arrangement generally shown as 78. The locking arrangement includes a ball 80 which is engaged in a portion of the handle post 72 and into the second slide 56. The ball 80 cannot move out of its engagement into the handle post 72 until a spool 82 has been moved distally against the resilient action of spring 83. Distal movement of the spool 82 is achieved by the distal end 84 of the first slide 54 engaging against the pin 86 of the spool 82. This action will be discussed in relation to FIG. 3C.

The mounting post 72 is mounted into the handle 52 by means of a screw thread 91 and locking pin 93 which acts to prevent relative rotation between the mounting post and the handle.

Figure 3A:
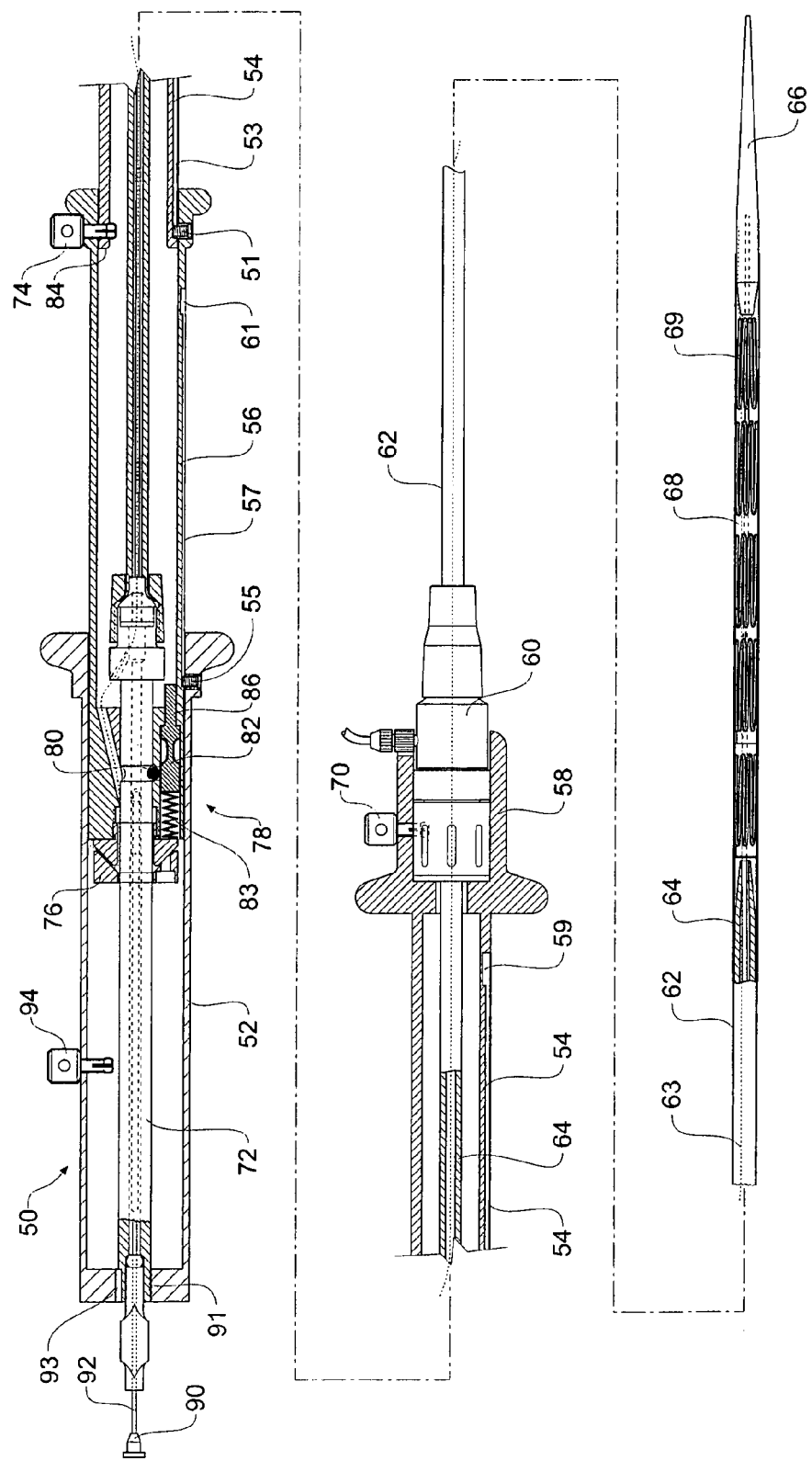
Figure 3B:
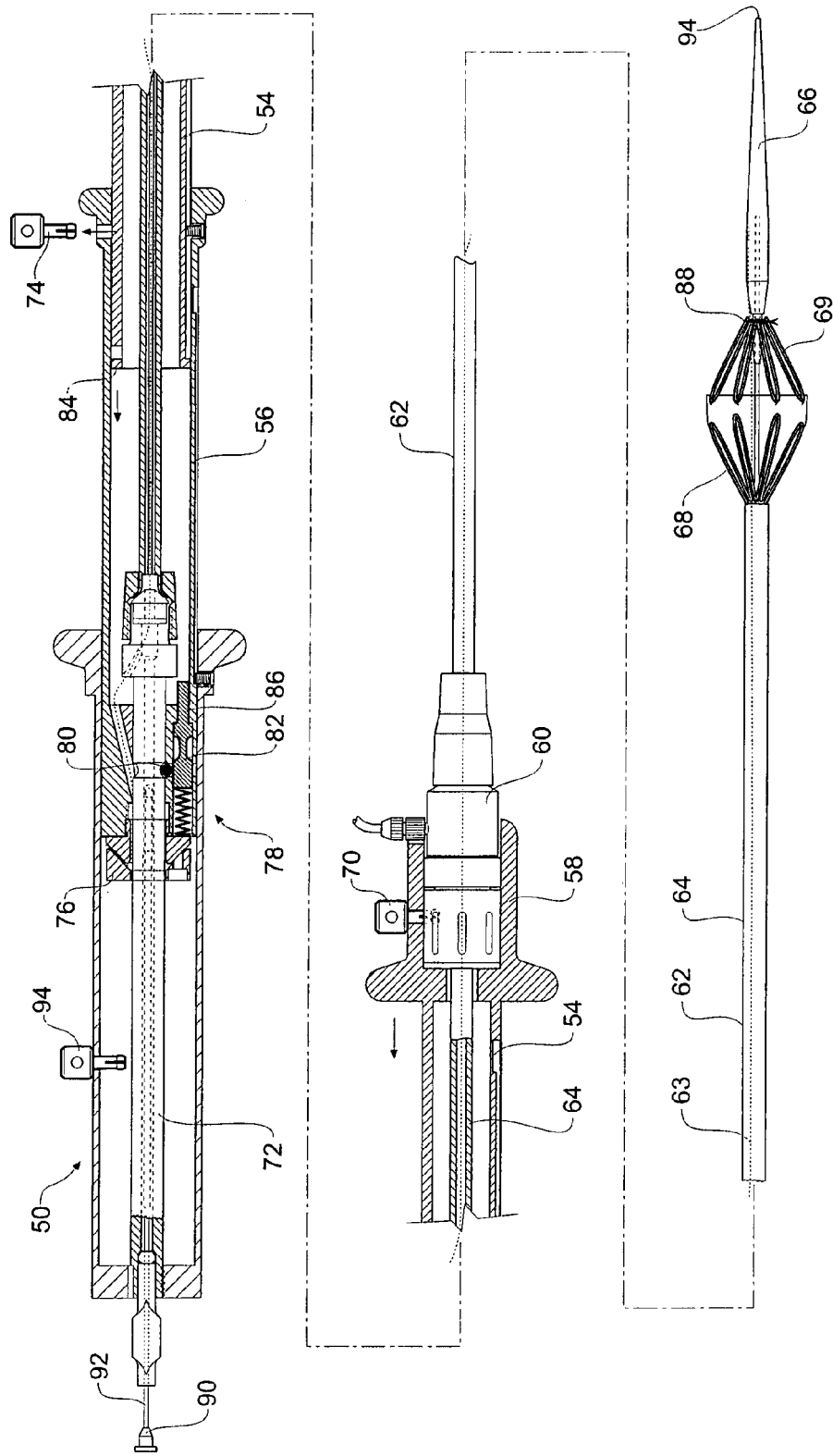

A first stage of operation of the stent graft introducer according to the present invention is shown in FIG. 3B. The locking pin 74 is withdrawn so that the first slide 54 can slide within the second slide 56. As the hub 60 is connected to the first slide 54, the hub and therefore the sheath 62 is withdrawn from the nose cone dilator 66 so that the stent graft 68 is partially exposed. At this stage, the proximal end 88 of the stent graft 68 is still retained just distal of the nose cone dilator 66. The Luer lock connector 90 can be used to enable the flushing of any foreign substance that may be present in the guide wire catheter 92 prior to insertion of the device onto a guide wire during deployment and where necessary to enable contrast fluids to be supplied through the guide wire catheter to exit at the proximal end 94 of the nose cone dilator 66 to enable an operator to inject contrast medium to assist with radiographic positioning of the stent graft during deployment.

Figure 3C:
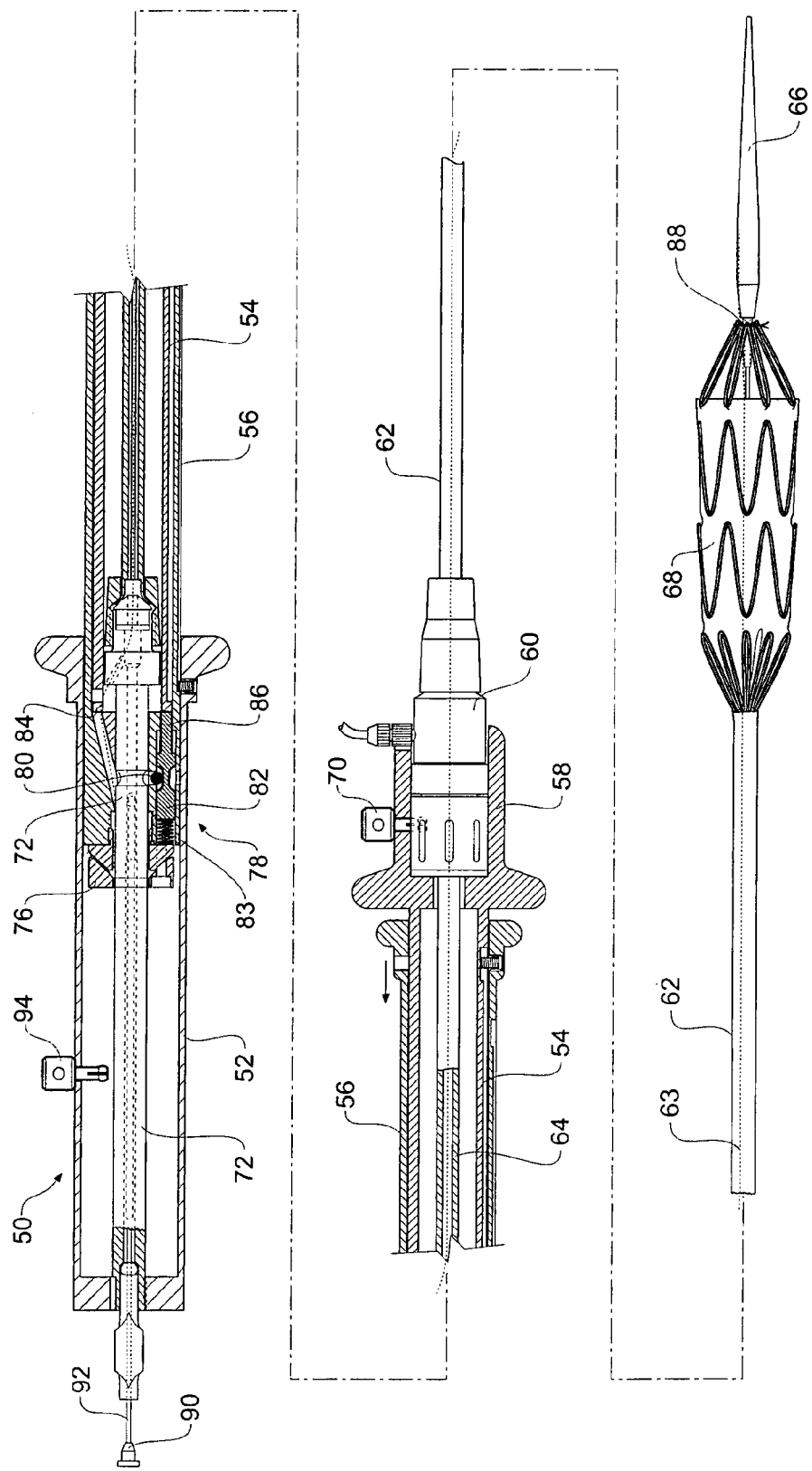

In the next stage as shown in FIG. 3C, the first slide 54 continues to slide back inside the second slide 56 until the distal end 84 of the first slide 54 engages the pin 86 of the lock mechanism 78. This moves the spool 82 against the spring 83 so the ball 80 can move out of its engagement with the handle post 72 which enables the second slide 56 to be able to move with respect to the handle portion 52.

At this stage, more of the stent graft 68 is exposed and the proximal end 88 is still retained just distal of the nose cone dilator 66.

Figure 3D:
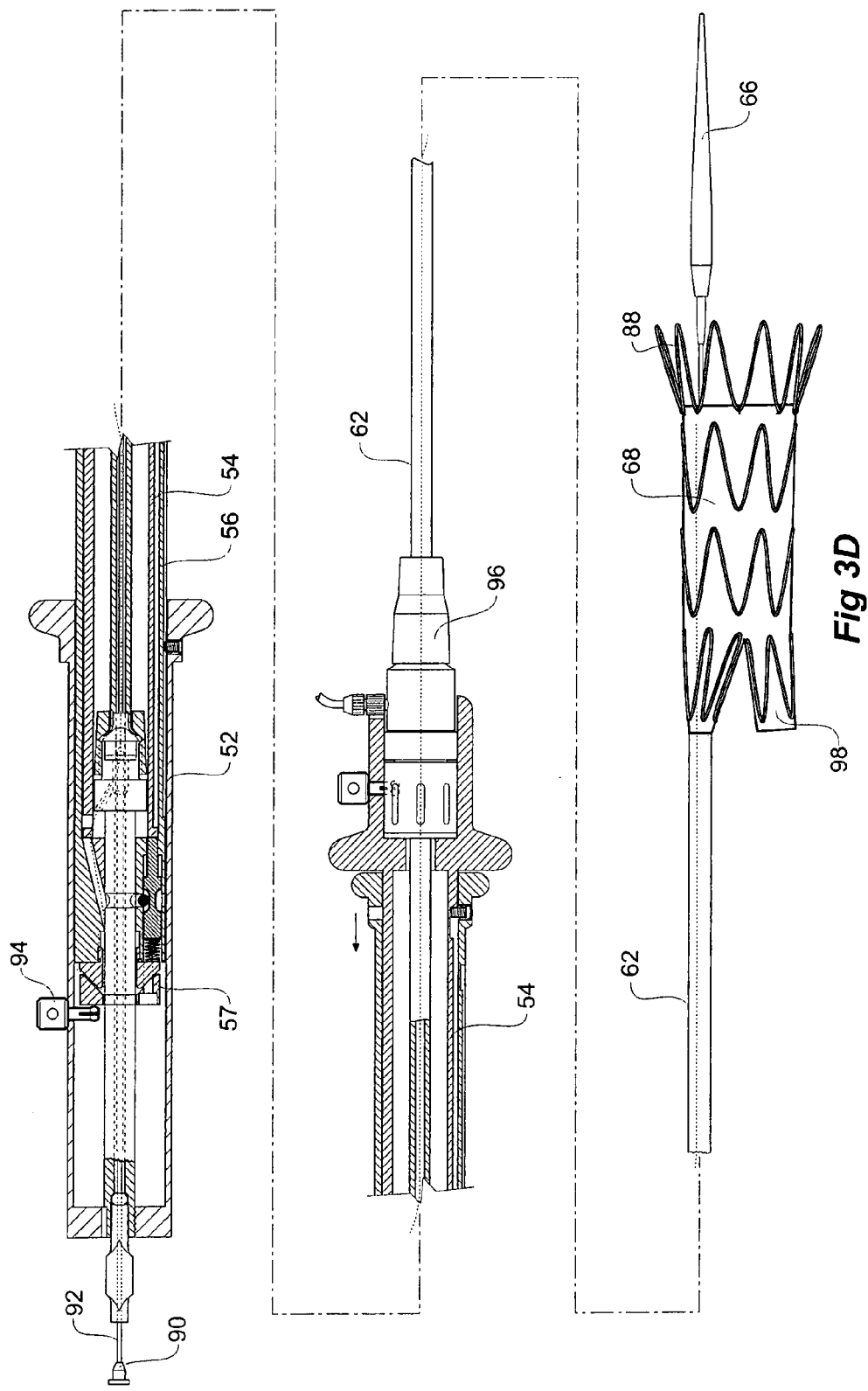

As shown in FIG. 3D, continued movement of the first slide 54 along with the second slide 56 within the handle portion 52 can occur until the distal end 57 of the second slide 56 engages locking pin 94.

At this stage, because the distal end of the trigger wires 63 are clamped by the trigger wire clamp 76 on the distal end of the second slide 56, movement of the second slide 56 has pulled the trigger wire 63 from its retention arrangement at the end 88 of the stent graft 68 so the proximal end 88 of the stent graft is freed, as shown in FIG. 3D. At the same time, the sheath 62 has been withdrawn so that while the main body of the stent graft 68 is still retained within the sheath, a side arm 98 has been released.

In some embodiments the distal end of the stent graft may also have a trigger wire retention system to retain the distal end of the stent graft onto the pusher catheter and the length of the distal retaining trigger wire may be such that at the stage shown in FIG. 3D the distal end of the stent graft is still retained by that trigger wire.

At this stage, a side arm can be deployed such as in relation to deployment about the aortic bifurcation by access from the contra-lateral iliac artery to engage an extension arm into the side arm 98. Our earlier PCT Patent Publication No. WO 98/53761 discussed above showed how such a deployment can be done.

The pin 94 can then be removed as shown in FIG. 3E and the first and second slides continued in their movement back into the handle portion 52. If there is a distal trigger wire, that wire can be released during this stage of the movement. Completion of the movement of the first and second slides 54 and 56 into the handle 52 ensures that the sheath 62 is completely withdrawn from the stent graft 68 and the stent graft 68 is released.

The locking pin 70 for the hub into the hub socket 58 on the first slide 54 can then be withdrawn so that the pusher 64 and nose cone dilator 66 can be withdrawn through the sleeve 62, along with the handle assembly, leaving the hub and sheath in place.

Subsequent deployment operations can be made through the sheath 62 and hub 60 as required.

It is desirable that there is no relative rotary motion between the first slide 54 and the second slide 56 and between the second slide 56 and the handle portion 52 so that no unwanted twisting of the stent graft occurs inside the patient during deployment. To ensure that there is no relative rotary motion between the first slide 54 and the second slide 56 and between the second slide 56 and the handle portion 52 there is a pin 51 on the second slide 56 which runs in a longitudinal groove 53 in the first slide 54. Similarly there is a pin 55 in the handle portion which runs in a groove 57 in the second slide 56.

It is also desirable that once there is complete retraction of the first slide 54 into the second slide 56 and complete retraction of the second slide 56 into the handle portion 52 that neither slide can be re-extended. To prevent re-extension the grooves 53 and 57 have a deeper recesses 59 and 61 respectively at their proximal ends and the pins 51 and 55 are spring loaded so that when they reach the end of their travel in the respective grooves the pins drop into the deeper recesses 59 and 61 such that the respective slides cannot be re-extended.

Figure 4:
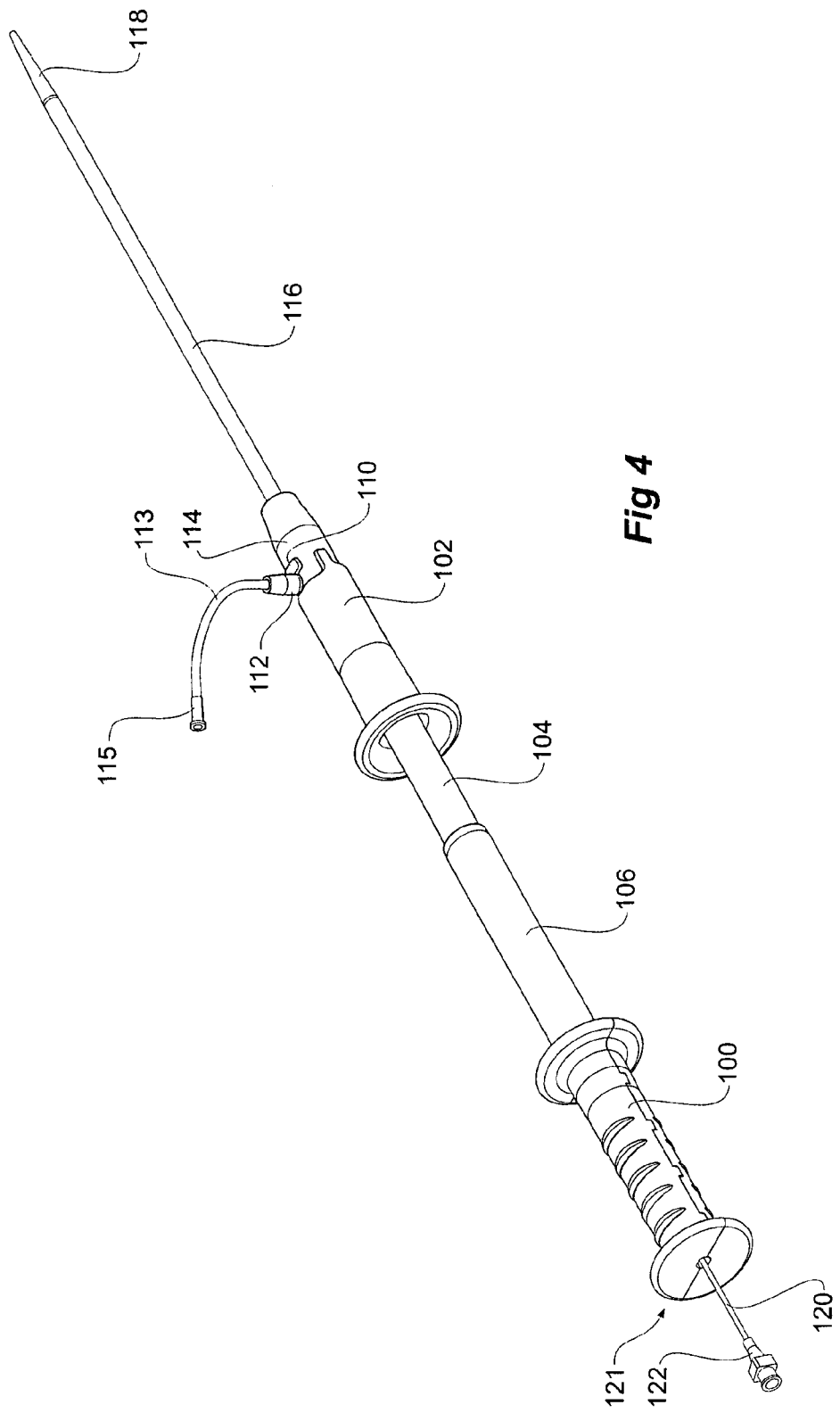
FIG. 4 shows an alternative embodiment of stent graft introducer according to the present invention.

FIG. 4 shows a still further embodiment of a stent graft introducer according to the present invention.

In this embodiment, the introducer includes a first handle portion 100, a hub retainer 102, a first slide 104 and a second slide 106. The hub retainer 102 mounts permanently onto the first slide 104 and the first slide 104 slides telescopically within the second slide 106 and the second slide 106 slides telescopically within the handle portion 100.

The hub retainer 102 includes a hook 110 which engages around a socket 112 for a side tube 113 on a hub 114 and thereby retains the hub 114 into the hub retainer 102. By relative rotation of the hub with respect to the hub retainer the hub can be disengaged from the hub retainer.

Extending from the hub is a sheath 116 which extends to a nose cone dilator 118 at the proximal end of the introducer and there is a pusher catheter within the sheath. The side tube 113 has a male Luer lock connector 115 which is primarily for the flushing of the internal cavity of the sheath 116 and hub 114 with heparin for the prevention of blood clotting as well as to remove air from within the graft and system prior to the introduction into the vasculature. Another useful effect is that the heparin offers a certain lubricating property that aids in the deployment of the system. During the deployment process if necessary contrast medium can be supplied between the sheath 116 and the pusher catheter (64 in FIG. 3A) of the introducer.

A guide wire catheter 120 extends out of the distal end 121 of the handle portion 100 and on the end of the guide wire catheter 120 is a male Luer lock connector 122 which enables contrast medium to be supplied through the guide wire catheter 120 to the nose cone dilator 118 of the introducer.

Figure 5A:
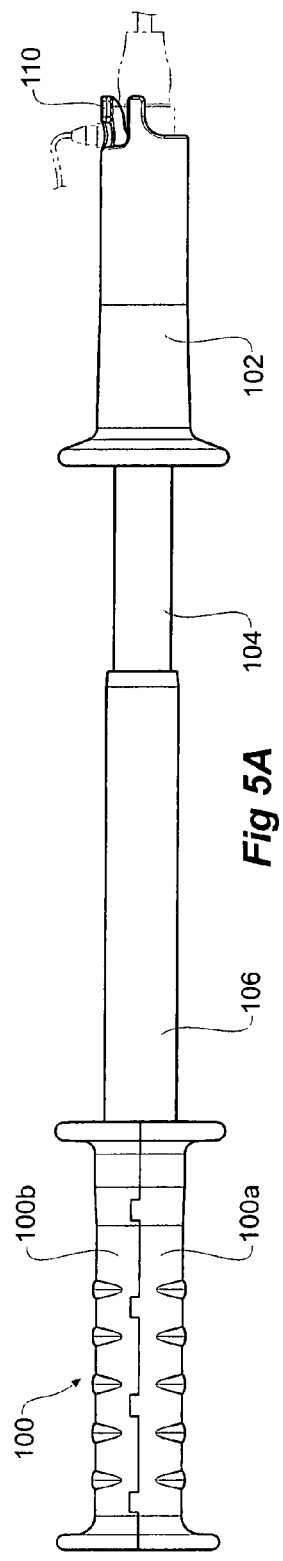
FIG. 5A shows a side view of the handle assembly portion of the embodiment shown in FIG. 4.
Figure 5B:
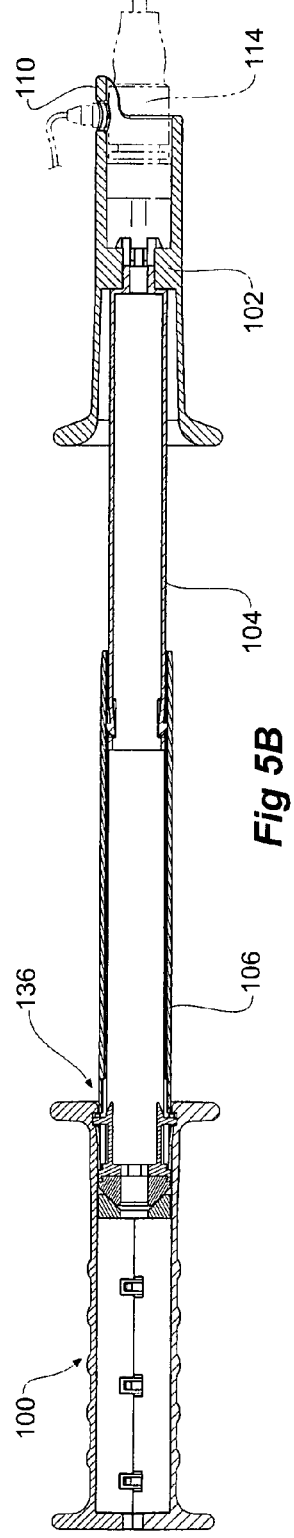
FIG. 5B shows a cross-sectional embodiment of the device shown in FIG. 5A.
Figure 5C:
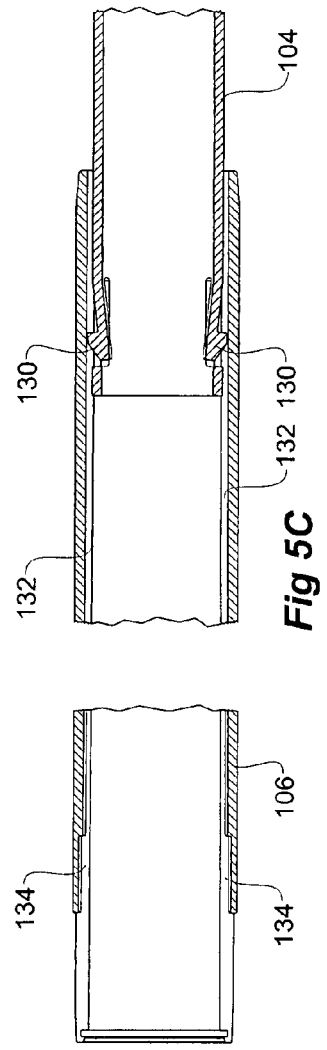
FIG. 5C shows a cross-section of part of the device of FIG. 4 showing detail of the anti-rotation and anti-re-extension portions of the device.

FIGS. 5A and 5B show a side view and a cross-sectional side view of the deployment device according to the embodiment shown in FIG. 4. FIG. 5C shows detail of the portion of engagement between the first slide 104 and the second slide 106 particularly showing how the fingers which prevent relative rotation of the first slide within the second slide engage.

It will be noted that in this embodiment the handle portion 100 is comprised of two portions 100a and 100b which are joined together to make the handle portion 100. Extending from the handle portion 100 is the second slide 106 and extending from the second slide 106 is the first slide 104. The hub retainer 102 is mounted on to the proximal end of the first slide 104. The hub 114 of a introducer is mounted into the hub retainer as discussed above.

As shown in detail in FIG. 5C a pair of resilient fingers 130 which are on the first slide 104 run in a track 132 on the inside of the second slide 106 to prevent relative rotation of the first slide with respect to the second slide. At the distal end of the second slide 106 the track 132 deepens to a recess 134 into which the spring arms 130 engage to prevent re-extension of the first slide.

The lock arrangement between the second slide 106 and handle arrangement 100 which prevents movement of the second slide 106 with respect to the handle portion 100 until the first slide portion 104 has fully retracted is shown generally as 136 in FIG. 5B and is shown in more detail in FIG. 6A.

In FIG. 6A it will be seen that the second slide 106 extends back into the handle portion 100 and at the distal end of the second slide 106 is an end cap 152 with a locking arrangement generally shown as 136 and a trigger wire clamp generally shown as 138. The locking arrangement includes a pair of resilient fingers 140 with locking pins 142 which engage into a groove 144 in the handle portion 100. In their rest position the pins 142 are engaged into the recess 144 to prevent relative movement of the second slide 106 with respect to the handle 100.

FIG. 6A also depicts in detail the arrangement by which relative rotation of the second slide 106 with respect to the handle is prevented. In this embodiment the mounting post 135 within the handle portion 100 has a flat 137 and the end cap 152 of the second slide 106 has a corresponding flat 139 so that the end cap 152 and hence the second slide 106 cannot rotate one with respect to the other. The mounting post 135 is mounted into the handle 100 by the mounting post having a special profile at its distal end and a corresponding profile is moulded into the distal ends handle portions 100a and 100b which are joined together to make the handle portion 100 so that when they are joined together they prevent relative rotation of the handle post with respect to the handle.

As shown in FIG. 6B as the first slide 104 is retracted or moved distally into the second slide 106 the distal end 146 of the first slide 104 approaches the spring loaded fingers 140.

Further distal movement of the first slide 104 into the second slide 106 as shown in FIG. 6C causes the distal end 146 to engage with the spring loaded fingers 140 to cause them to deflect inwards such that the pin 142 is withdrawn from the recess 144 in the handle. Continued movement distally of the first slide 104 therefore also causes movement of the second slide 106 and both move distally together.

Now looking again at FIG. 6A it will be noted that the trigger wire clamp arrangement 138 includes a first clamping portion 150 which is received on the end cap 152 of the second slide 106 and a second clamping portion 154 which is screwed by means of screw 156 onto the first portion 150. The trigger wire or wires 158 are clamped between the first clamping portion 150 and second clamping portion 154 to retain them in place.

It will be noted from FIG. 6A that the trigger wire extends through the lumen 160 of the pusher catheter 162 and back through the connection with the handle post 164 and outside of the handle post back to the clamp arrangement 138.

After the locking arrangement 136 has been released as illustrated in FIG. 6C the trigger wire clamp moves distally with the second slide 106 and as discussed above in relation to FIG. 3 the trigger wire releases at least the proximal end of the stent graft.

FIG. 6E shows the handle portion 100 at the stage after the locking arrangement has been released and the first and second slides and the locking arrangement 136 move together distally within the handle portion 100 until the locking pins 142 engage into a relatively shallow recess 150 on the inside surface of the handle portion. This temporarily stops distal movement. Hence this recess 150 provides an equivalent feature to the third stop 94 shown in FIG. 3D.

At this stage the sheath 116 has been withdrawn so that while the main body of the stent graft is still retained within the sheath a side arm of the stent graft has been released. An extension arm can be deployed into the side arm while the main stent graft is secured to the introducer by the sheath covering the stent graft distal of the bifurcation.

Further movement of the first slide distally releases the locking pins 142 from the recess 150 because of engagement of the first slide with the resilient fingers 140 and the assembly of the first and second slides and the locking arrangement 136 can together continue to move distally until the locking pins 142 engage into the deeper recess 152. This stops distal movement and the depth of the recess 152 prevents the locking pins from escaping the recess and thereby prevents the re-extension of the introduction assembly. Hence the recess 152 provides an equivalent feature to the recess 61 shown in FIG. 3A.

Figure 7:
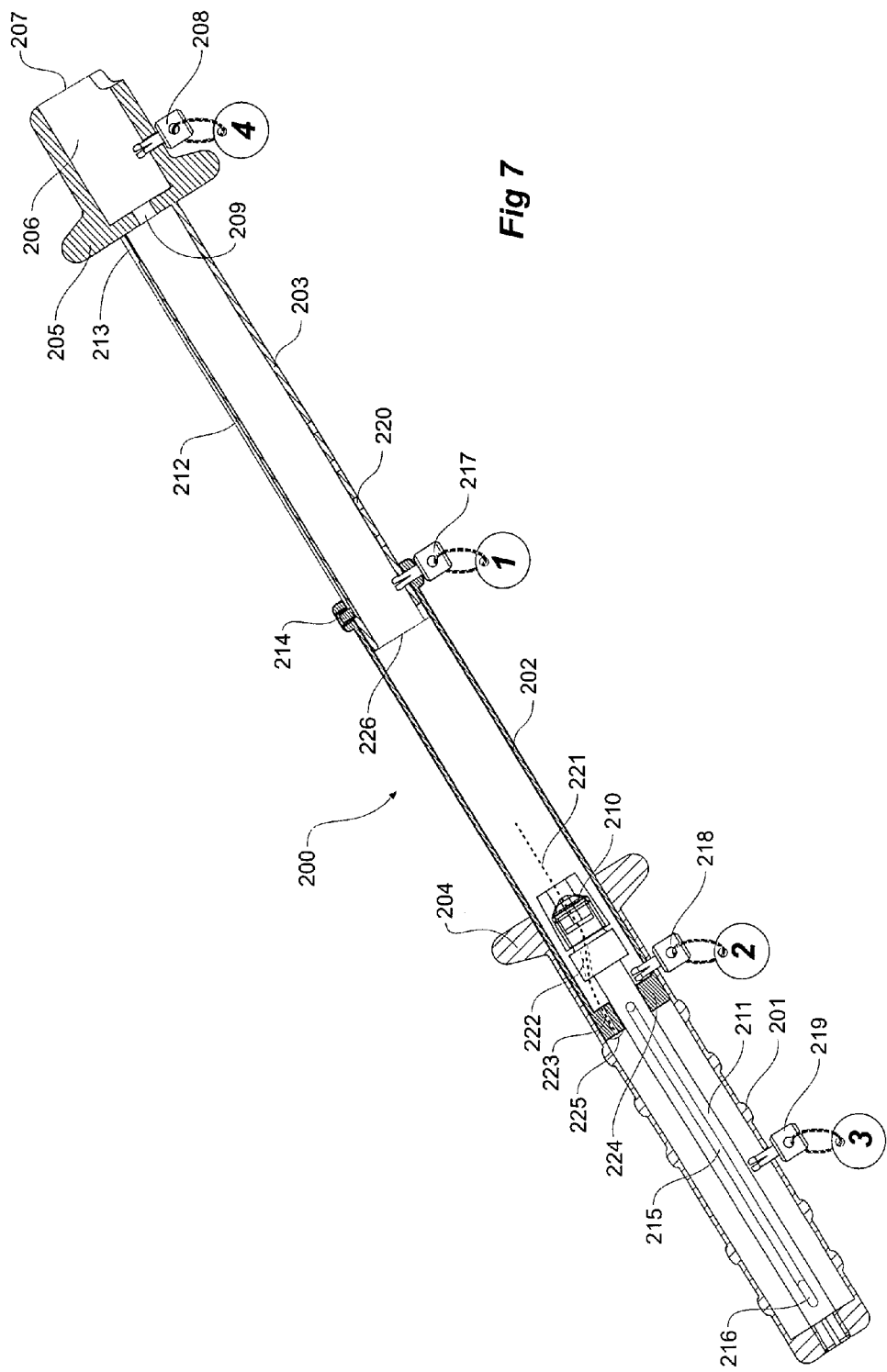
FIG. 7 shows and alternate embodiment of actuation assembly according to the present invention.

FIG. 7 shows an alternate embodiment of an actuation assembly for a stent graft introduction arrangement according to the invention. In this embodiment the actuation assembly 200 comprises a fixed handle 201, a release portion 202 and a sliding handle 203. A first hand grip 204 is on the fixed handle and a second hand grip is on the sliding handle 205. A hub retainer 206 is on the proximal end 207 of the actuation assembly. A hub locking pin 208 engages through the hub retainer 206 into a hub (eg 60 in FIG. 3A) to retain an introducer part of the device (not shown) into the actuator assembly. The pusher of the introducer (64 in FIG. 3A) extends through the aperture 209 in the hub retainer and extends back to the fastening nut 210 on the handle post 211 within the handle 201.

Groove 212 and recess 213 in the sliding handle acted on by the spring loaded pin 214 provide the means to prevent relative rotation and re-extension respectively for the sliding handle with respect to the release portion. Groove 215 and recess 216 in the handle post 211 acted on by a spring loaded pin (not shown) on the release portion provide the means to prevent relative rotation and re-extension respectively for the fixed handle with respect to the release portion.

A first removable stop pin 217 extends through apertures in the release portion 202 and the sliding handle 203 to prevent the sliding handle from telescoping into the release portion until it is removed. A second removable stop pin 218 extends through apertures in the release portion 202 and the fixed handle 201 to prevent the release portion from telescoping into the fixed handle until it is removed. A third removable stop pin 219 extends through an aperture in the wall of the handle portion and prevents full retraction of the release portion 202 into the fixed handle until it is removed.

The removable stop pins are numbered 1 to 4 to indicate the order in which they are intended to be released.

The sliding handle 203 includes apertures 220 in the same longitudinal line with the aperture through which passes the removable stop pin 217. These apertures provide alternative positions for the removable stop pin 184 through the sliding handle to allow for different lengths of stent graft mounted onto the introducer.

Trigger wires 221 (equivalent to 63 in FIG. 3A) extend through the pusher and fastening nut 210 and exit the post 211 through aperture 222. From there they pass through aperture 223 in the distal end 224 of the release portion 202 and are affixed thereto by a set screw 225.

The process of use of the actuation assembly of this embodiment is as follows. The operator first removes the first removable stop pin 217 (Numbered 1) and slides the sliding handle 203 back into the release portion 202. This starts withdrawal of the sheath from the stent graft on the introducer. Movement stops when the distal end 226 of the sliding handle 203 engages the distal end of the release portion 224. At this stage the sheath is partially withdrawn from the stent graft but the proximal end of the stent has not been released. The operator can then remove the second removable stop pin 218 (Numbered 2) and then the release portion and the sliding handle can together slide back into the fixed handle. This action withdraws the trigger wires from the proximal retention of the stent graft on the introducer and releases a side arm or short leg of a stent graft. A leg extension can be deployed into the short leg while the stent graft is secured to the introducer by the sheath still covering the stent graft distal of the bifurcation. After successful deployment of the leg extension the removable stop pin 219 (Numbered 3) can be removed and the release portion and the sliding handle can together slide further back into the fixed handle. This further sliding fully removes the sheath from the stent graft (and the distal retention if used). At this stage either the combination of the actuator assembly and introducer can be removed from the patient together or the hub locking pin 208 (Numbered 4) can be withdraw to enable the actuator assembly and the pusher to be removed from the patient while leaving the hub and sheath in place to enable further procedures if required.

FIG. 8 shows several views of an embodiment of pin suitable for the stop between the first slide and the second slide. The pin 230 has a grip portion 232 and a shank 234. The shank is bifurcated and has a lower protrusion 235 which provides a degree of resilience and resistance to removal of the pin when the pin is placed into a suitable sized aperture. Extending from the shank 234 are a pair of fingers 236 which can deflect into a recess 238 in the side of the shank 234. The fingers 236 in their undeflected position prevent removal of the pin from an aperture into which the shank is placed but when deflected into the recess 238 the fingers do not prevent removal.

It will be noted that the shank 234 is non-circular in cross section so that the pin can only be placed into an aperture in a selected orientation which means that the fingers will be directed, in use, in the direction from which an action to deflect them will come.

FIGS. 9A to 9D show the various stage of the slide action using the pin shown in FIG. 8. The components of the actuation assembly for a stent graft introduction arrangement according to this embodiment of the invention are the same as shown in FIG. 7 and the same reference numerals are used for corresponding items.

In this embodiment the actuation assembly as shown in FIG. 9A comprises a fixed handle 201, a release portion 202 and a sliding handle 203. A first hand grip 204 is on the fixed handle. The release portion 202 cannot slide with respect to the handle fixed 201 because the pin 230 extends through apertures in both the fixed handle 201 and the release portion 202. The pin cannot be withdrawn because the fingers 236 engage the inside of the release portion 202. As shown in FIG. 9B as the sliding handle 203 is retracted into the release portion 202 it engages the fingers 236 in the shank 234 of the pin 230. Further retraction of the sliding handle 203 into the release portion 202 deflects the fingers 236 into the recess 238 as shown in FIG. 9C. The pin 230 can then be removed as shown in FIG. 9D which enables the sliding handle 203 and the release portion 202 to together retract into the fixed handle.

Figure 10:
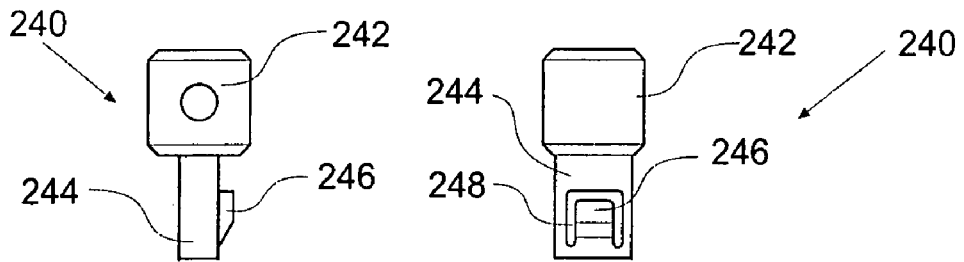
FIG. 10 shows an alternative embodiment of pin suitable for the stop between the first slide and the second slide.

FIG. 10 shows several views of an alternative embodiment of pin suitable for the stop between the first slide and the second slide. The pin 240 has a grip portion 242 and a shank 244. The shank is substantially rectangular in cross section. Extending from a long side of the shank 244 is a deflectable protrusion 246 which can be deflect into a recess 248 in the side of the shank 244. The protrusion 246 in its undeflected position prevents removal of the pin from an aperture into which the shank is placed but when deflected into the recess 248 the fingers do not prevent removal.

It will be noted that the shank 244 is rectangular in cross section so that the pin can only be placed into an aperture in a selected orientation which means that the fingers will be directed, in use, in the direction from which an action to deflect them will come.

Figure 11A:
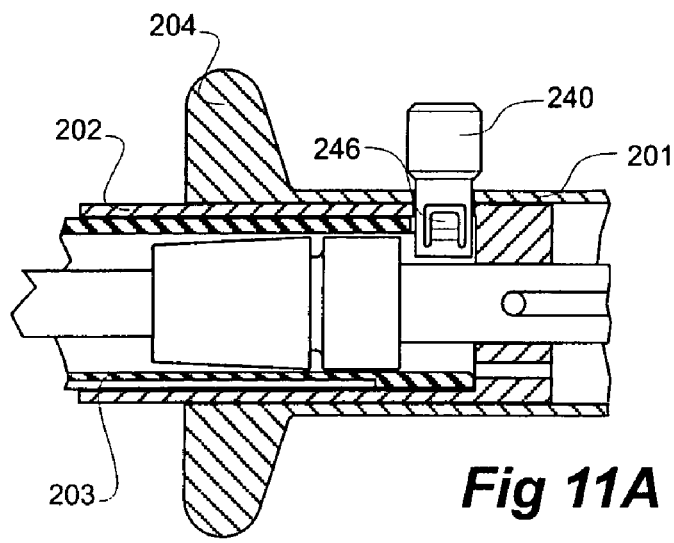
FIGS. 11A and 11B show a stage of the slide action using the pin shown in FIG. 10.
Figure 11B:
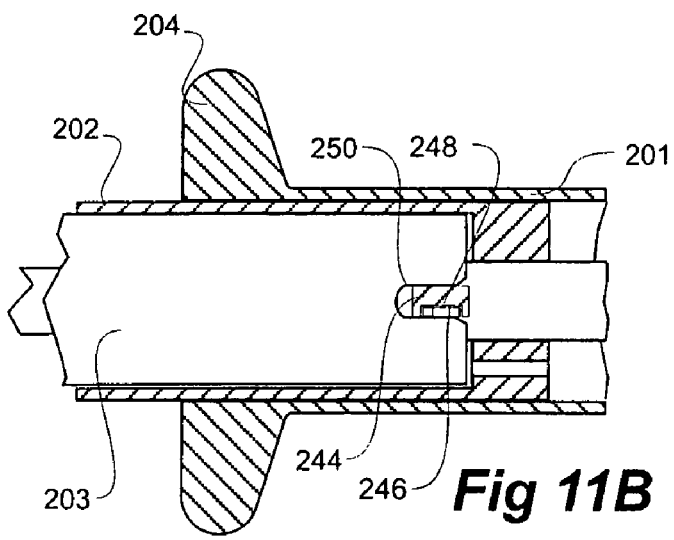

FIGS. 11A and 11B show a stage of the slide action using the pin shown in FIG. 10. The components of the actuation assembly for a stent graft introduction arrangement according to this embodiment of the invention are the same as shown in FIG. 7 and the same reference numerals are used for corresponding items.

In this embodiment the actuation assembly as shown comprises a fixed handle 201, a release portion 202 and a sliding handle 203. A first hand grip 204 is on the fixed handle. The release portion 202 cannot slide with respect to the handle fixed 201 because the pin 240 extends through apertures in both the fixed handle 201 and the release portion 202. The pin cannot be withdrawn because the protrusion 246 engages the inside of the release portion 202. As shown in FIG. 11B as the sliding handle 203 is retracted into the release portion 202a recess 250 in the end of the sliding handle 203 engages around the protrusion 246 on the shank 244 of the pin 240 and deflects the protrusion 246 into the recess 248 in the shank 244. The pin 240 can then be removed which enables the sliding handle 203 and the release portion 202 to together retract into the fixed handle 201.

Throughout this specification various indications have been given as to the scope of the invention but the invention is not limited to any one of these but may reside in two or more combined together. The examples are given for illustration only and not for limitation.

What is claimed is:

1. A stent graft introducer comprising a deployment catheter and a handle assembly; the deployment catheter comprising a pusher, a stent graft releasably retained onto the pusher, a temporary stent graft retention arrangement, a sheath coaxially around the pusher and enclosing the stent graft and a sheath hub to which the sheath is mounted; the handle assembly comprising, a handle, a first slide and a second slide, the first slide able to slide to retract within the second slide and the second slide able to slide to retract within the handle, the first slide including a releasable engagement arrangement to engage and retain the sheath hub thereon, a first removable stop arrangement engaged between the handle and the second slide to prevent relative movement thereof, the pusher extending longitudinally through the first and second slides and being mounted to the handle, the temporary stent graft retention arrangement including trigger wires extending through the pusher and being affixed to the second slide; whereby movement of the first slide with respect to the second slide moves the sheath hub and thereby the sheath on the pusher to expose the stent graft until the first slide engages against the first removable stop arrangement, the first removable stop arrangement being automatically actuated by engagement of the first slide with the first removable stop arrangement to disengage the first removable stop arrangement from the handle and whereupon removal of the first removable stop arrangement the second slide can move with respect to the handle thereby withdrawing the trigger wires and releasing the temporary stent graft retention arrangement.

2. A stent graft introducer as in claim 1 comprising a second removable stop arrangement between the first slide and the second slide to prevent relative movement thereof until it is removed.

3. A stent graft introducer as in claim 1 including a third removable stop arrangement between the handle and the second slide to restrict the distance of retraction of the second slide into the handle until the third removable stop arrangement has been removed.

4. A stent graft introducer as in claim 1 wherein the first removable stop arrangement engaged between the handle and the second slide comprises a catch on the second slide engaged into a recess on the handle and the catch is disengaged by the first slide engaging against the catch upon complete retraction of the first slide into the second slide.

5. A stent graft introducer as in claim 1 further including means to prevent relative rotation of the first slide with respect to the second slide.

6. A stent graft introducer as in claim 1 further including means to prevent re-extension of the first slide with respect to the second slide after complete retraction.

7. A stent graft introducer as in claim 1 further including means to prevent relative rotation of the second slide with respect to the handle.

8. A stent graft introducer as in claim 1 further including means to prevent re-extension of the second slide with respect to the handle after complete retraction.

9. A stent graft introducer actuation assembly comprising a fixed handle, a release portion and a sliding handle, the release portion telescoping within the fixed handle and the sliding handle telescoping within the release portion, a sheath hub being retained to the sliding handle and a pusher extending from the fixed handle through the release portion and the sliding handle, a first stop to prevent movement of the sliding handle with respect to the release portion and a second stop to prevent movement of the release portion with respect to the fixed handle, the second stop being automatically actuated by engagement of the sliding handle with the second stop.

10. A stent graft introducer actuation assembly as in claim 9 including a third stop acting between the fixed handle and the release portion to restrict the distance of retraction of the release portion into the fixed handle until the third stop is removed.

11. A stent graft introducer actuation assembly as in claim 9 wherein the fixed handle includes a first grip and the sliding handle includes a second grip.

12. A stent graft introducer actuation assembly as in claim 9 further including means to prevent relative rotation of the sliding handle with respect to the release portion.

13. A stent graft introducer actuation assembly as in claim 9 further including means to prevent re-extension of the sliding handle with respect to the release portion after complete retraction of the sliding handle into the release portion.

14. A stent graft introducer actuation assembly as in claim 9 further including means to prevent relative rotation of the release portion with respect to the fixed handle.

15. A stent graft introducer actuation assembly as in claim 9 further including means to prevent re-extension of the release portion with respect to fixed the handle after complete retraction of the release portion into the fixed handle.

16. A stent graft introducer actuation assembly comprising a fixed handle, a release portion and a sliding handle, the release portion telescoping within the fixed handle and the sliding handle telescoping within the release portion, the sheath hub being retained to the sliding handle and the pusher extending from the fixed handle through the release portion and the sliding handle, a first stop to prevent movement of the sliding handle with respect to the release portion and a second stop to prevent movement of the release portion with respect to the fixed handle, a third stop acting between the fixed handle and the release portion to restrict the distance of retraction of the release portion into the fixed handle until the third stop pin is removed, the second stop being automatically actuated by engagement of the first slide with the second stop to disengage the second stop from the handle, the fixed handle including a first grip and the sliding handle including a second grip, means to prevent relative rotation of the sliding handle with respect to the release portion, means to prevent re-extension of the sliding handle with respect to the release portion after complete retraction of the sliding handle into the release portion, means to prevent relative rotation of the release portion with respect to the fixed handle and means to prevent re-extension of the release portion with respect to fixed the handle after complete retraction of the release portion into the fixed handle.

* * * * *